US010520430B2

(12) United States Patent
Yamazaki

(10) Patent No.: US 10,520,430 B2
(45) Date of Patent: Dec. 31, 2019

(54) INFORMATION PROCESSING APPARATUS AND INFORMATION PROCESSING METHOD

(71) Applicant: SONY CORPORATION, Tokyo (JP)

(72) Inventor: Tomohiro Yamazaki, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 94 days.

(21) Appl. No.: 15/328,778

(22) PCT Filed: Jun. 19, 2015

(86) PCT No.: PCT/JP2015/067731
§ 371 (c)(1),
(2) Date: Jan. 24, 2017

(87) PCT Pub. No.: WO2016/021313
PCT Pub. Date: Feb. 11, 2016

(65) Prior Publication Data
US 2017/0227459 A1 Aug. 10, 2017

(30) Foreign Application Priority Data
Aug. 8, 2014 (JP) .................. 2014-163067

(51) Int. Cl.
*G01B 11/06* (2006.01)
*G01N 21/47* (2006.01)
(Continued)

(52) U.S. Cl.
CPC ............ *G01N 21/47* (2013.01); *G01B 17/00* (2013.01); *G01H 9/00* (2013.01); *G02B 27/48* (2013.01);
(Continued)

(58) Field of Classification Search
None
See application file for complete search history.

(56) References Cited

U.S. PATENT DOCUMENTS 7,775,113 B2 * 8/2010 Bakish .............. G01H 9/00
398/130
2003/0019931 A1 * 1/2003 Tsikos .............. G02B 26/10
235/454
(Continued)

FOREIGN PATENT DOCUMENTS

| JP | 62-156563 A | 7/1987 |
| JP | 07-055464   | 3/1995 |

(Continued)

OTHER PUBLICATIONS

Philippe Clemenceau, Sebastien Breugnot, Laurent Collot, "Polarization diversity active imaging," Proc. SPIE 3380, Laser Radar Technology and Applications III, (Sep. 8, 1998); (Year: 1998).*

(Continued)

*Primary Examiner* — Clifford Hilaire
(74) *Attorney, Agent, or Firm* — Chip Law Group

(57) ABSTRACT

A speckle pattern is effectively utilized. An information processing apparatus is an information processing apparatus including a light output unit and an acquisition unit. The light output unit included in the information processing apparatus is for outputting a plurality of light beams for generating a speckle pattern, to a plurality of locations of objects which are within an imaging range. Also, the acquisition unit included in the information processing apparatus is for acquiring the speckle patterns formed by scattering of the plurality of light beams striking the plurality of locations on a location-by-location basis.

15 Claims, 11 Drawing Sheets

(51) Int. Cl.

| | | |
|---|---|---|
| G01H 9/00 | (2006.01) | |
| H04N 5/222 | (2006.01) | |
| H04N 5/225 | (2006.01) | |
| H04N 5/33 | (2006.01) | |
| H04N 5/232 | (2006.01) | |
| H04N 5/77 | (2006.01) | |
| H04N 9/04 | (2006.01) | |
| G06T 7/521 | (2017.01) | |
| G01B 17/00 | (2006.01) | |
| G02B 27/48 | (2006.01) | |
| H04N 5/235 | (2006.01) | |
| H04N 9/07 | (2006.01) | |

(52) U.S. Cl.
CPC ........... *G06T 7/521* (2017.01); *H04N 5/2226* (2013.01); *H04N 5/2256* (2013.01); *H04N 5/232* (2013.01); *H04N 5/2353* (2013.01); *H04N 5/23212* (2013.01); *H04N 5/332* (2013.01); *H04N 5/77* (2013.01); *H04N 5/772* (2013.01); *H04N 9/045* (2013.01); *H04N 9/07* (2013.01)

(56) References Cited

U.S. PATENT DOCUMENTS

2005/0024624 A1* 2/2005 Gruhlke ................. G01P 3/36
356/3.01
2010/0226543 A1 9/2010 Zalevsky et al.
2011/0190612 A1* 8/2011 McKenna ............ A61B 5/0059
600/323
2012/0162631 A1 6/2012 Hutchin
2015/0248161 A1* 9/2015 Komori ................. G06F 3/016
345/157

FOREIGN PATENT DOCUMENTS

| JP | 2001-133320 A | 5/2001 |
| JP | 2005-283160 A | 10/2005 |
| JP | 2008-051553 A | 3/2008 |
| JP | 2010-216908 A | 9/2010 |
| JP | 2013-179466 A | 9/2013 |
| JP | 2014-055860 A | 3/2014 |

OTHER PUBLICATIONS

Jin X, Li C, Wang LV. Effects of acoustic heterogeneities on transcranial brain imaging with microwave-induced thermoacoustic tomography. Medical physics. Jul. 2008;35(7Part1):3205-14. (Year: 2008).*

Nippolainen E, Semenov DV, Kamshilin AA, Belyaev AV, Andreev SV, Gurevich BS. Fast distance sensing by use of the speckle effect. InOptical Measurement Systems for Industrial Inspection IV Jun. 13, 2005 (vol. 5856, pp. 691-697). International Society for Optics and Photonics. (Year: 2005).*

Semenov, et al., "An Ultra-Fast Distance Sensor Based on Dynamic Speckles Generated by Acousto-Optic Deflection", Measurement Science and Technology, 2006 IOP Publishing Ltd, vol. 17, No. 11, stacks.iop.org/MST/17/2906, pp. 2906-2912.

* cited by examiner

FIG. 7

|   |   |   |   |   |   |   |   |
|---|---|---|---|---|---|---|---|
| R | IR | R | IR | R | IR | R | IR |
| IR | B | IR | B | IR | B | IR | B |
| R | IR | R | IR | R | IR | R | IR |
| IR | B | IR | B | IR | B | IR | B |
| R | IR | R | IR | R | IR | R | IR |
| IR | B | IR | B | IR | B | IR | B |

116

INFORMATION PROCESSING APPARATUS AND INFORMATION PROCESSING METHOD

CROSS REFERENCE TO RELATED APPLICATIONS

This application is a U.S. National Phase of International Patent Application No. PCT/JP2015/067731 filed on Jun. 19, 2015, which claims priority benefit of Japanese Patent Application No. JP 2014-163067 filed in the Japan Patent Office on Aug. 8, 2014. Each of the above-referenced applications is hereby incorporated herein by reference in its entirety.

TECHNICAL FIELD

The present technology relates to information processing apparatuses. More particularly, the present technology relates to an information processing apparatus and information processing method which dealt with a speckle pattern, and a program for causing a computer to execute the method.

BACKGROUND ART

Conventional techniques of performing various kinds of analysis by utilizing scattering of light striking an object have been proposed. For example, a technique of applying in-phase light (highly coherent light (e.g., laser light)) to a rough surface, and acquiring a grainy pattern (speckle pattern) formed by the scattered light, to perform various kinds of analysis, has been proposed (e.g., Patent Literature 1). For example, by acquiring a speckle pattern and then analyzing an oscillation in the speckle pattern, sound data generated from the rough surface can be acquired.

CITATION LIST

Patent Literature

Patent Literature 1: US 2010/0226543A

DISCLOSURE OF INVENTION

Technical Problem

According to the above conventional technique, sound data can be acquired on the basis of an oscillation in a speckle pattern. Therefore, for example, sound data of a specific object of interest which is remotely located can be acquired. Here, it is considered that if sound data of a plurality of specific objects of interest which are remotely located can be acquired, the sound data can be more effectively utilized. In other words, it is considered that if speckle patterns occurring at a plurality of locations can be acquired and subject to various kinds of analysis, the speckle patterns can be more effectively utilized.

With the above in mind, the present technology has been made. It is an object of the present technology to effectively utilize a speckle pattern.

Solution to Problem

The present technology has been made to solve the above problem. A first aspect of the present technology is an information processing apparatus, and information processing method, and a program causing a computer to execute the method. The information processing apparatus includes: a light output unit configured to output a plurality of light beams for generating speckle patterns, to a plurality of locations of objects which are within an imaging range; and an acquisition unit configured to acquire the speckle patterns formed by scattering of the plurality of light beams striking the plurality of locations, on a location-by-location basis. As a result, achieved is the effect of outputting a plurality of light beams for generating a speckle pattern, to a plurality of locations of objects which are within an imaging range, and acquiring the speckle patterns formed by scattering of the plurality of light beams striking the plurality of locations on a location-by-location basis.

According to the first aspect, the light output unit may output a single beam of light that is output from a light source, as the plurality of light beams by using a diffractive optical element. As a result, achieved is the effect of outputting a single beam of light from a light source as a plurality of light beams using a diffractive optical element.

According to the first aspect, the light output unit may output a plurality of laser beams by using a laser array as a light source. As a result, achieved is the effect of outputting a plurality of laser beams using a laser array as a light source.

According to the first aspect, the light output unit may use a surface-emitting laser array as the laser array. As a result, achieved is the effect of outputting a plurality of laser beams using a surface-emitting laser array as a light source.

According to the first aspect, the light output unit may output the plurality of laser beams having different wavelengths from the laser array, and the acquisition unit may acquire the speckle patterns by using an image sensor capable of acquiring color information. As a result, achieved is the effect of outputting a plurality of laser beams having different wavelengths from a laser array, and acquiring speckle patterns using an image sensor capable of acquiring color information.

According to the first aspect, the light output unit may output the plurality of laser beams having different polarization directions from the laser array, and the acquisition unit may acquire the speckle patterns by using an image sensor capable of acquiring polarization information. As a result, achieved is the effect of outputting a plurality of laser beams having different polarization directions from a laser array, and acquiring speckle patterns using an image sensor capable of acquiring polarization information.

According to the first aspect, the light output unit may modulate the plurality of light beams and output the plurality of modulated light beams from the light source. As a result, achieved is the effect of modulating a plurality of light beams and outputting the plurality of modulated light beams from a light source.

According to the first aspect, the plurality of locations may be arranged in the entirety or a portion of the imaging range. As a result, achieved is the effect of arranging a plurality of locations in the entirety or a portion of an imaging range.

According to the first aspect, the information processing apparatus may further include: a control unit configured to acquire at least one of sound data and distance information related to the object on the basis of the acquired speckle pattern. As a result, achieved is the effect of acquiring at least one of sound data and distance information related to an object on the basis of an acquired speckle pattern.

According to the first aspect, the information processing apparatus may further include: an imaging unit configured to image the object to generate image data; and a control unit configured to acquire at least one of sound data and distance information related to the object on the basis of the acquired speckle pattern. The control unit may perform auto focus control on the imaging unit on the basis of at least one of the acquired sound data and the acquired distance information. As a result, achieved is the effect of performing auto focus control on the imaging unit on the basis of the acquired at least one of the sound data and the distance information.

According to the first aspect, the information processing apparatus may further include: an imaging unit configured to image the object to generate image data; and a control unit configured to acquire at least one of sound data and distance information related to the object on the basis of the acquired speckle pattern. The control unit may perform exposure control on the imaging unit on the basis of at least one of the acquired sound data and the acquired distance information. As a result, achieved is the effect of performing exposure control on an imaging unit on the basis of at least one of the sound data and the distance information that has been acquired.

According to the first aspect, the information processing apparatus may further include: a sound acquisition unit configured to acquire sound data around the information processing apparatus on the basis of vibration of a substance; and a control unit configured to acquire sound data related to the object on the basis of the acquired speckle pattern, and calculate a distance between the information processing apparatus and the object on the basis of the sound data related to the object and the sound data acquired by the sound acquisition unit. As a result, achieved is the effect of acquiring sound data related to an object on the basis of an acquired speckle pattern, and calculating a distance between an information processing apparatus and the object on the basis of this sound data and sound data acquired by a sound acquisition unit.

A second aspect of the present technology is an information processing apparatus, and information processing method, and a program causing a computer to execute the method. The information processing apparatus includes: a control unit configured to calculate a distance between the information processing apparatus and an object which is within an imaging range, on the basis of sound data related to the object acquired on the basis of a speckle pattern formed by scattering of light striking the object, and sound data related to the object acquired on the basis of vibration of a substance. As a result, achieved is the effect of calculating a distance between an information processing apparatus and an object, on the basis of sound data acquired on the basis of a speckle pattern, and sound data acquired on the basis of vibration of a substance.

A third aspect of the present technology is an information processing apparatus, and information processing method, and a program causing a computer to execute the method. The information processing apparatus includes: a control unit configured to acquire and output sounds generated at a plurality of locations of objects which are within an imaging range on a location-by-location basis, on the basis of speckle patterns formed by scattering of light beams striking the plurality of locations. As a result, achieved is the effect of acquiring and outputting sounds generated at a plurality of locations on a location-by-location basis, on the basis of speckle patterns formed by scattering of light beams striking the objects.

Also, in the third aspect, if an operation of selecting a desired location from the plurality of locations has been received, the control unit may acquire and output only a sound generated at the selected location. As a result, achieved is the effect of, if an operation of selecting a desired location from a plurality of locations has been received, acquiring and outputting only a sound generated at the selected location.

Advantageous Effects of Invention

According to the present technology, the excellent effect of effectively utilizing a speckle pattern can be exhibited. Note that the effects described here are not necessarily limited, and any effect that is desired to be described in the present disclosure may be exhibited.

BRIEF DESCRIPTION OF DRAWINGS

FIG. 7 is a diagram showing an arrangement example of light sources of a surface-emitting laser array 115 in an embodiment of the present technology.

FIG. 10(a) and FIG. 10 (b) is a diagram showing a relationship example between laser light output from an information processing apparatus 100 and objects in an embodiment of the present technology.

FIG. 11(a) and FIG. 11 (b) is a diagram showing a relationship example between laser light output from an information processing apparatus 100 and objects in an embodiment of the present technology.

MODE(S) FOR CARRYING OUT THE INVENTION

A mode for carrying out the present technology (hereinafter referred to as an "embodiment") will now be described. The description will be provided in the following order. 1.

Embodiment (example in which speckle patterns occurring at a plurality of locations are acquired)

<1. Embodiment>

[Example of Use of Information Processing Apparatus]

Figure 1:
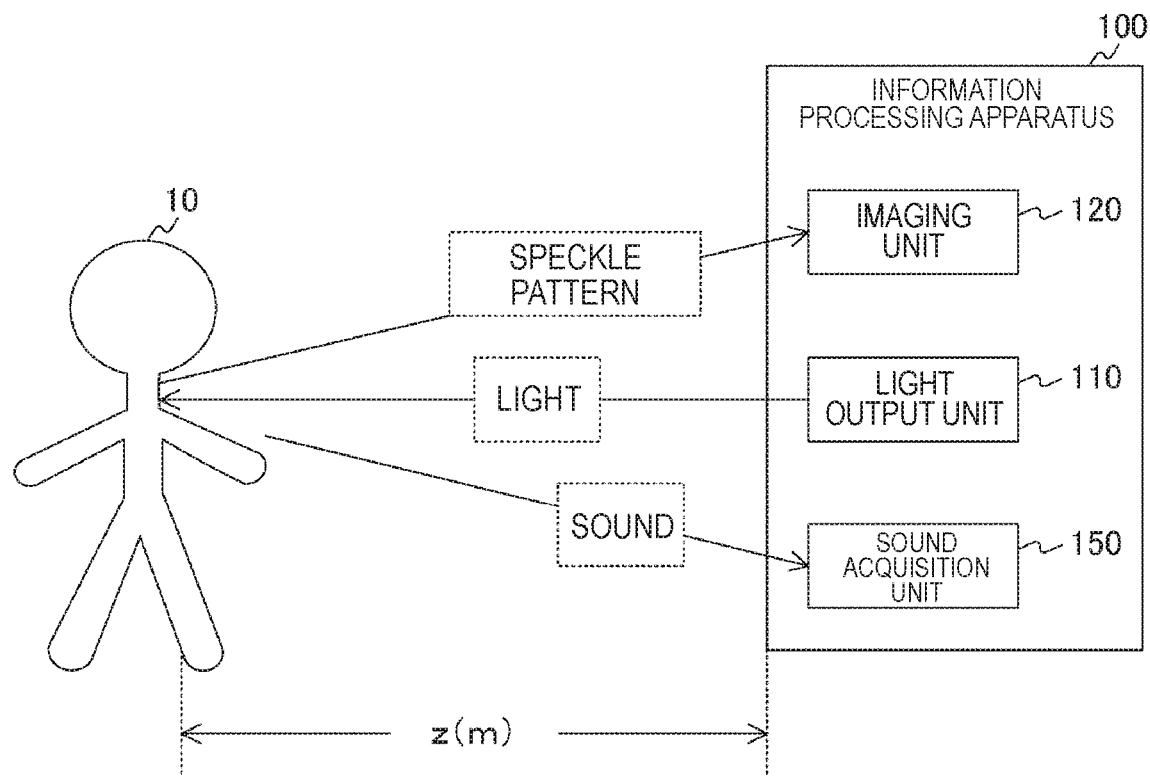
FIG. 1 is a diagram showing an example of use of an information processing apparatus 100 in an embodiment of the present technology.

FIG. 1 is a diagram showing an example of use of an information processing apparatus 100 in an embodiment of the present technology.

The information processing apparatus 100 outputs highly coherent light (e.g., laser light) to a person 10 from a light output unit 110, and acquires a speckle pattern formed by the scattered light using an imaging unit 120. Thereafter, the information processing apparatus 100 can acquire various kinds of information (e.g., sound data, distance information) on the basis of an oscillation in the acquired speckle pattern.

Here, as the highly coherent light, highly directional light can be used, for example. Therefore, a specific sound emitted by an object relatively far away from the information processing apparatus 100 can be acquired. For example, even when there is a relatively large distance between the information processing apparatus 100 and the person 10, a sound (voice) uttered by the person 10 can be acquired by outputting highly directional laser light from the light output unit 110 toward the throat of the person 10.

Also, a sound acquisition unit 150 acquires a sound around the information processing apparatus 100 on the basis of vibration of a substance (e.g., air, water). Thus, the information processing apparatus 100 can acquire distance information on the basis of information (sound data) about the sound acquired by the sound acquisition unit 150, and the speckle pattern acquired by the imaging unit 120.

Specifically, a distance (object distance) from the information processing apparatus 100 to an object 10 can be calculated on the basis of the result of comparison between the sound data acquired by the sound acquisition unit 150 and sound data acquired on the basis of the speckle pattern acquired by the imaging unit 120.

Here, in order to acquire sound data on the basis of the speckle pattern acquired by the imaging unit 120, light which is output from the light output unit 110 and then scattered is utilized. Also, the speed c1 of light is $2.99 \times 10^8$ m/s. Therefore, as to the sound data acquired on the basis of the speckle pattern acquired by the imaging unit 120, it can be assumed that a time (delay time dt1) it takes a sound emitted by the object 10 to reach the information processing apparatus 100 is substantially zero (i.e., dt1~0).

Meanwhile, in order to acquire sound data by the sound acquisition unit 150, the sound acquisition unit 150 acquires sound data on the basis of vibration of air which depends on a sound emitted by the object 10. Also, the speed c2 of sound is 340 m/s. Therefore, as to the sound data acquired by the sound acquisition unit 150, a time (delay time dt2) it takes a sound emitted by the object 10 to reach the information processing apparatus 100 is greater than zero.

Specifically, when a distance between the object 10 and the information processing apparatus 100 is represented by z (m), the delay time dt2 an be calculated by dividing the distance z between the object 10 and the information processing apparatus 100 by the sound speed c2. In other words, dt2=z/c2. Therefore, the distance between the object 10 and the information processing apparatus 100 can be calculated using the following expression:

$$z = c2 \times dt2 \quad (1)$$

Here, the delay time dt2 can be calculated on the basis of the result of comparison between the sound data acquired by the sound acquisition unit 150 and the sound data acquired on the basis of the speckle pattern acquired by the imaging unit 120. In other words, the distance z between the object 10 and the information processing apparatus 100 can be calculated on the basis of a difference between time (dt1) at which the object 10 emits some sound and a time (dt2) it takes that sound to reach the information processing apparatus 100.

Here, a method for determining whether or not there is a match between the sound data acquired by the sound acquisition unit 150 and the sound data acquired on the basis of the speckle pattern acquired by the imaging unit 120. For example, a control unit 190 (shown in FIG. 4) extracts a characteristic amount from the sound data acquired by the sound acquisition unit 150, and extracts a characteristic amount from the sound data acquired on the basis of the speckle pattern acquired by the imaging unit 120. Thereafter, the control unit 190 calculates a similarity by comparing these extracted characteristic amounts with each other. Thereafter, if the calculated similarity exceeds a threshold, the control unit 190 determines that the two sounds which have a similarity exceeding the threshold are the same.

For example, each piece of sound data is sampled and converted into digital data by an analog/digital (A/D) conversion process. Also, the digital data is subjected to a process such as frequency analysis or the like at appropriate time intervals, and thereby converted into parameters representing a spectrum or other acoustic characteristics of a speech. As a result, a time-series characteristic amount related to a speech is extracted. Thereafter, a matching process is performed on the extracted time-series characteristic amount, and a determination result is output as the result of the matching process. Note that various other known techniques may be used as the speech analysis method and the speech recognition method.

Thus, sound data can be obtained on the basis of an oscillation in a speckle pattern formed by scattered beams of highly coherent light, such as laser light or the like, which is applied to a rough surface. Such use of highly directional light allows for acquisition of sound data of a specific object of interest remotely located. Also, if sound data can be acquired from a plurality of objects of interest while the concurrence of information can be maintained and a decrease in information amount is prevented, it is convenient. In other words, it is considered that if speckle patterns occurring at a plurality of locations can be acquired and used in various kinds of analysis, the speckle patterns can be more effectively utilized.

With the above in mind, an example of effective utilization of a speckle pattern is shown in the embodiment of the present technology.

[Configuration Example of Imaging Unit]

Figure 2:
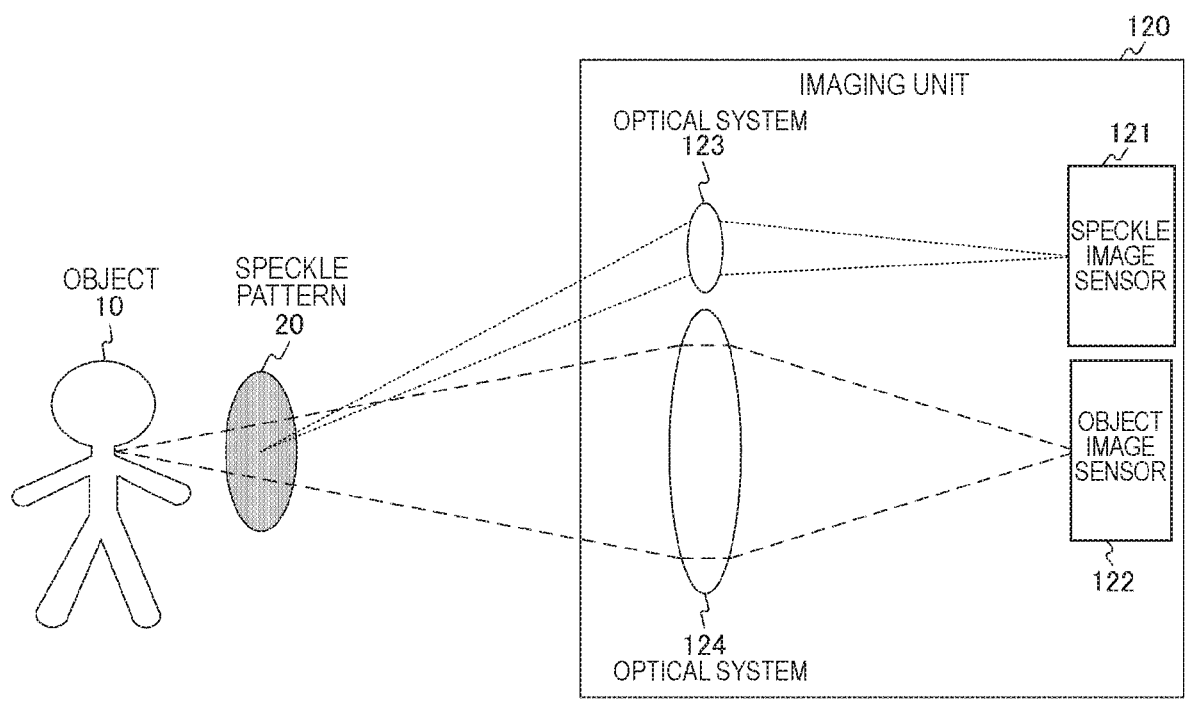
FIG. 2 is a diagram showing an internal configuration example of an imaging unit 120 in an embodiment of the present technology.

FIG. 2 is a diagram showing an internal configuration example of the imaging unit 120 in the embodiment of the present technology. FIG. 2 shows an imaging unit example including two optical systems 123 and 124.

Figure 3:
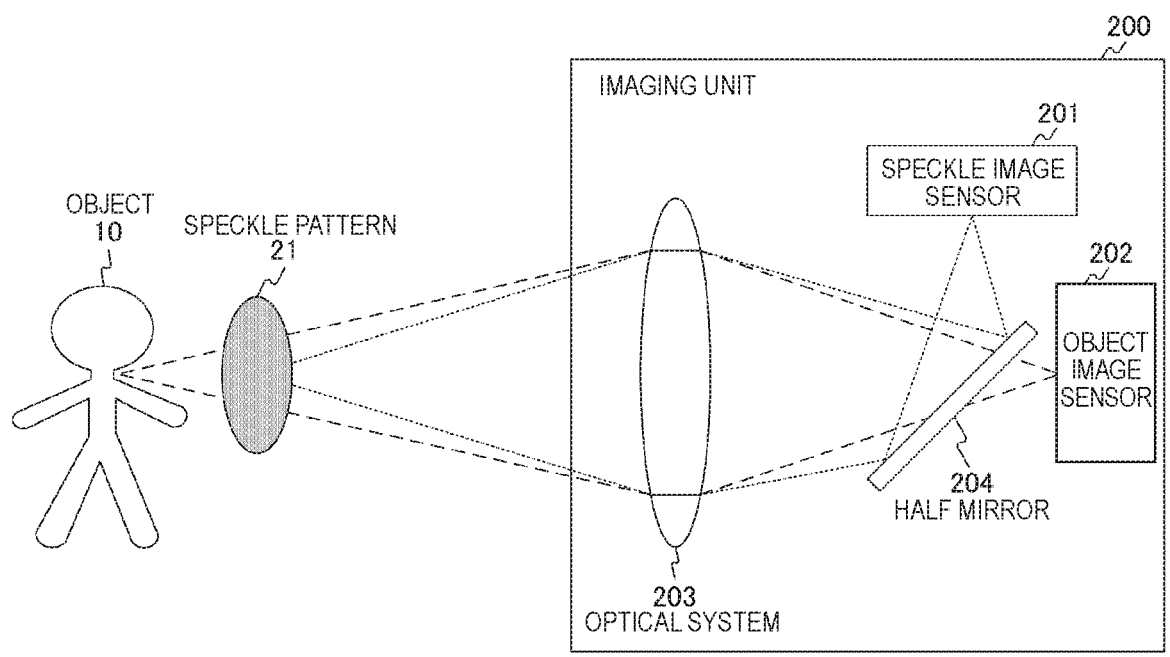
FIG. 3 is a diagram showing an internal configuration example of an imaging unit 200 in an embodiment of the present technology.

FIG. 3 is a diagram showing an internal configuration example of an imaging unit 200 in the embodiment of the present technology. FIG. 3 shows a variation of the imaging unit 120 shown in FIG. 2. Specifically, shown is an imaging unit example including a single optical system 203 and a half mirror 204.

The imaging unit 120 shown in FIG. 2 includes a speckle image sensor 121, an object image sensor 122, and the optical systems 123 and 124.

The speckle image sensor 121 is an image sensor for receiving light entering through the optical system 123 and generating image data. Also, the object image sensor 122 is an image sensor for receiving light entering through optical system 124 and generating image data. Note that, as these image sensors, a charge coupled device (CCD) image sensor or a complementary metal oxide semiconductor (CMOS) image sensor can be used, for example. Note that the speckle image sensor 121 is an example of an acquisition unit described in the accompanying claims.

The optical systems 123 and 124 include a plurality of lenses (e.g., a zoom lens, a focusing lens) for bringing light from an object into focus. Also, light from an object which is brought into focus by the optical system 123 enters the speckle image sensor 121. Also, light from an object which is brought into focus by the optical system 124 enters the object image sensor 122.

Here, the object image sensor 122 is different from the speckle image sensor 121 in that the object image sensor 122 generates image data to be recorded, while the speckle image sensor 121 generates image data of a speckle pattern 20 of scattered beams of light output from the light output unit 110.

Here, the speckle pattern 20 of the object 10 is formed before the object 10 (closer to the information processing apparatus 100). Therefore, the object 10 and the speckle pattern 20 have different focal point positions. Therefore, in order to simultaneously acquire an image of the object 10 and an image of the speckle pattern 20 (speckle image), it is necessary for the information processing apparatus 100 to include optical systems for providing the different focal point positions. FIG. 2 shows an example in which the information processing apparatus 100 includes the different optical systems 123 and 124. Also, FIG. 3 shows an example in which the information processing apparatus 100 includes the single optical system 203 and the half mirror 204, and uses the half mirror 204 to shift the focal point position of light which is brought into focus by the single optical system 203.

For example, when laser light is applied to an object having a rough surface (e.g., the skin of a person), a speckle pattern is formed by reflection of the light. Specifically, light beams of the laser light scattered from positions on the surface of the object are superposed together. Thus, the superposition of light beams having different phases forms a speckle pattern.

Also, the laser light reflected from the object spreads out more as it goes away from the object. Therefore, it is preferable to acquire a speckle pattern which is formed closer to the information processing apparatus 100 than to the object. For example, when the distance between the information processing apparatus 100 and an object of interest is 5 m, a speckle pattern which is formed at a position which is about 1 m away from the object of interest can be acquired and used.

Also, a speckle pattern is wave-like information, whose motion is recognized as an oscillation, and the oscillation is converted into a signal, which is used. For example, laser reflected from a moving portion of an object (e.g., a portion of the throat when a voice is uttered) moves on a speckle pattern. This movement can be recognized as an oscillation. Also, an acquired speckle pattern can be used for modification of an object, speech analysis, vibration analysis, or the like. For example, when sound data is acquired on the basis of an acquired speckle pattern, sound data can be acquired by a matching process between an oscillation in the acquired speckle pattern and vibration information for identifying sound data.

The imaging unit 200 shown in FIG. 3 includes a speckle image sensor 201, an object image sensor 202, the optical system 203, and the half mirror 204.

The speckle image sensor 201 and the object image sensor 202 correspond to the speckle image sensor 121 and the object image sensor 122 shown in FIG. 2.

The optical system 203 includes a plurality of lenses (e.g., a zoom lens, a focusing lens) for bringing light from an object into focus.

The half mirror 204 is a half-silvered mirror which transmits a portion of light collected by the optical system 203 so that the portion of light enters the object image sensor 202, and reflects the other portion of the light so that the other portion of the light enters the speckle image sensor 201. Specifically, the half mirror 204 transmits light from the object 10 which is a portion of light collected by the optical system 203 so that the light from the object 10 enters the object image sensor 202. Also, the half mirror 204 reflects scattered beams (corresponding to a speckle pattern 21) of light (e.g., laser light) output from the light output unit 110 which is a portion of light collected by the optical system 203 so that the scattered light enters the speckle image sensor 201.

[Configuration Example of Information Processing Apparatus]

Figure 4:
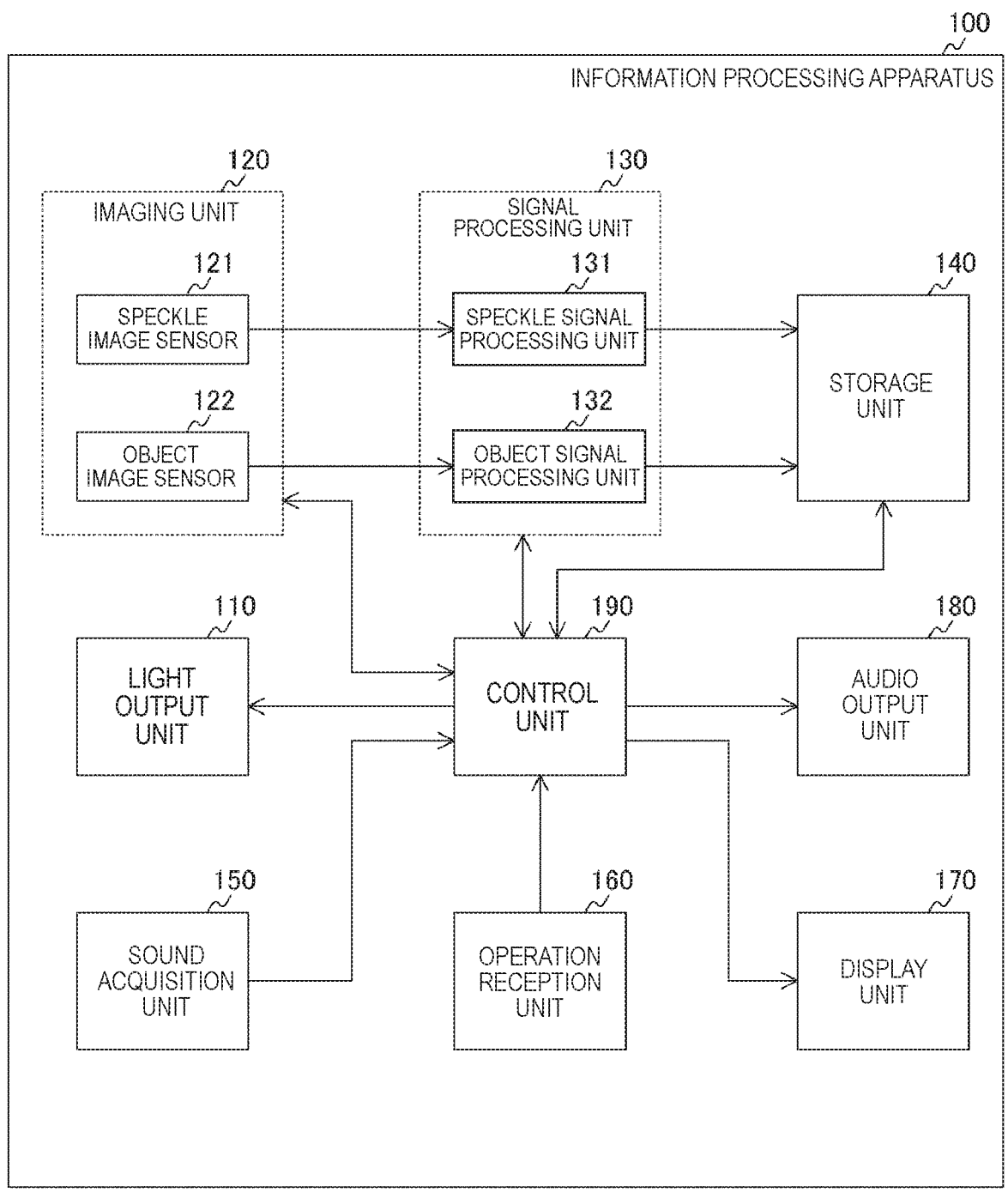
FIG. 4 is a block diagram showing a functional configuration example of an information processing apparatus 100 in an embodiment of the present technology.

FIG. 4 is a block diagram showing a functional configuration example of the information processing apparatus 100 in the embodiment of the present technology.

The information processing apparatus 100 includes the light output unit 110, the imaging unit 120, a signal processing unit 130, a storage unit 140, the sound acquisition unit 150, an operation reception unit 160, a display unit 170, an audio output unit 180, and the control unit 190.

The light output unit 110 outputs highly coherent light (e.g., laser light) under the control of the control unit 190. An output example of light by the light output unit 110 will be described in detail with reference to FIG. 5 and FIG. 6.

The imaging unit 120 images an object of interest to generate image data, and outputs the generated image data to the signal processing unit 130, under the control of the control unit 190. Specifically, the imaging unit 120 includes the speckle image sensor 121 and the object image sensor 122. Note that although the imaging unit 120 includes optical systems (e.g., the optical systems 123, 124, and 203) as shown in FIG. 2 and FIG. 3, the optical systems are not shown in FIG. 4.

Here, the size of image data generated by the speckle image sensor 121 can be smaller than the size of image data generated by the object image sensor 122. For example, the size of image data generated by the object image sensor 122 can be of full high definition (HD) (1920×1080 pixels). In this case, for example, the size of image data generated by the speckle image sensor 121 can be reduced to Video Graphics Array (VGA) (640×480 pixels) or approximately VGA.

Also, because the image data generated by the speckle image sensor 121 is used for acquisition of sound data, it is necessary for the image data generated by the speckle image sensor 121 to have a higher frame rate than that of the image data generated by the object image sensor 122. For example, the image data generated by the object image sensor 122 may have a frame rate of 30 to 60 frames per second (fps). In this case, for example, the image data generated by the speckle image sensor 121 may have a frame rate of about several thousands to several tens of thousands of fps.

The signal processing unit 130 performs various signal processes on the image data generated by the imaging unit 120, and records into the storage unit 140 the image data which has been subjected to the signal processes, under the control of the control unit 190.

Specifically, the signal processing unit 130 includes a speckle signal processing unit 131 and an object signal processing unit 132. The object signal processing unit 132 performs various signal processes on the image data (e.g., moving image data) generated by the object image sensor 122. Thereafter, the object signal processing unit 132 outputs to the control unit 190 the image data which has been subjected to the signal processes, and records that image data as an image content (e.g., a moving image file) into the storage unit 140.

The speckle signal processing unit 131 performs various signal processes on the image data (image data of a speckle pattern) generated by the speckle image sensor 121. Thereafter, the speckle signal processing unit 131 outputs to the control unit 190 the image data which has been subjected to the signal processes, and records into the storage unit 140 that image data (e.g., a moving image file) as accompanying information, in association with the image content that is simultaneously generated.

The storage unit 140 is a recording medium into which each item of information is stored under the control of the control unit 190. For example, the storage unit 140 stores image data which has been generated by the object image sensor 122 and then subjected to signal processes by the object signal processing unit 132, as an image content (e.g., a moving image file). Also, for example, the storage unit 140 stores image data (image data of a speckle pattern) which has been generated by the speckle image sensor 121 and then subjected to signal processes by the speckle signal processing unit 131, as accompanying information, in association with the image content.

The sound acquisition unit 150 acquires information (sound data) about a sound around the information processing apparatus 100, and outputs the acquired sound data to the control unit 190. For example, the sound acquisition unit 150 can acquire information (sound data) about a sound around the information processing apparatus 100 on the basis of vibration of a substance (e.g., air, water). Note that the sound acquisition unit 150 is implemented by, for example, a microphone.

The operation reception unit 160 is an operation reception unit which receives an operation performed by the user, and outputs control information (operation information) corresponding to the received operation, to the control unit 190. Note that the operation reception unit 160 is implemented by, for example, an operation member, such as a button, switch, or the like.

The display unit 170 displays various images under the control of the control unit 190. The display unit 170 is implemented by, for example, a display panel, such as a liquid crystal display (LCD), electroluminescence (EL) panel, or the like.

Note that at least a portion of the operation reception unit 160 and the display unit 170 may be integrally configured. For example, the operation reception unit 160 and the display unit 170 can be configured as a capacitive (capacitance type) touchscreen which detects touch or proximity of a conductive object (e.g., a finger of a person) on the basis of a change in capacitance.

The audio output unit 180 outputs sound data under the control of the control unit 190. The audio output unit 180 is implemented by, for example, a loudspeaker.

The control unit 190 controls each unit in the information processing apparatus 100 according to a control program. For example, the control unit 190 controls an imaging operation so that pieces of image data generated by the imaging unit 120 are sequentially recorded into the storage unit 140. Also, for example, the control unit 190 performs a playback process on an image content stored in the storage unit 140.

Also, for example, the control unit 190 generates and acquires sound data related to an object which is within an imaging range on the basis of image data of a speckle pattern.

Also, for example, the control unit 190 calculates a distance between the information processing apparatus 100 and a target included in the object, on the basis of the sound data related to the object acquired on the basis of image data of a speckle pattern and the sound data acquired by the sound acquisition unit 150. Note that the control unit 190 may acquire at least one of the sound data and the distance information.

[Output Example of Laser Light]

Figure 5:
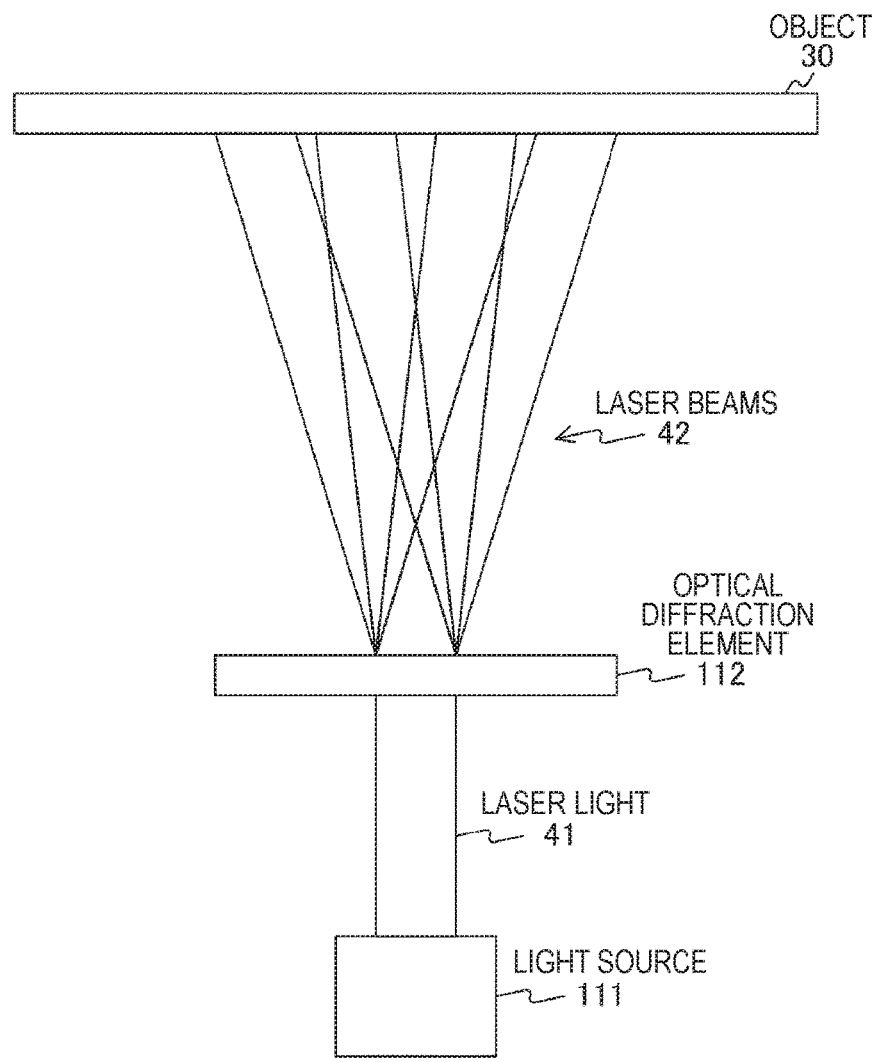
FIG. 5 is a diagram showing a configuration example for outputting a plurality of light beams from a light output unit 110 in an embodiment of the present technology.
Figure 6:
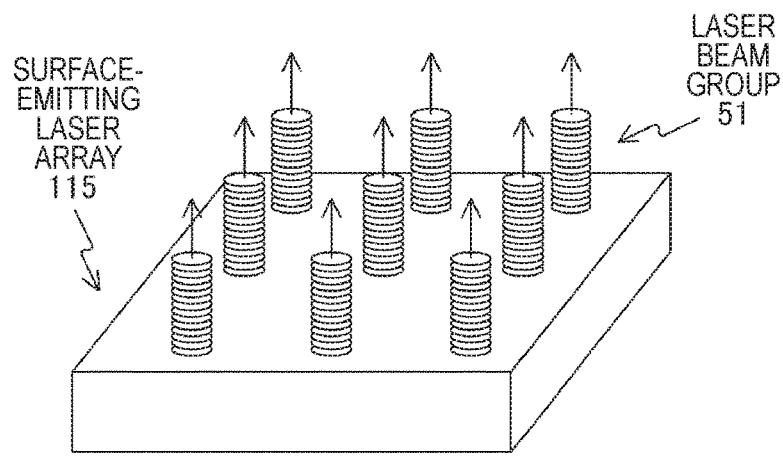
FIG. 6 is a diagram showing a configuration example for outputting a plurality of light beams from a light output unit 110 in an embodiment of the present technology.

FIG. 5 and FIG. 6 are diagrams showing configuration examples for outputting a plurality of light beams from the light output unit 110 in the embodiment of the present technology. Note that, in FIG. 5 and FIG. 6, each configuration shown is simplified for the sake of simplicity.

FIG. 5 shows an example in which laser light output from a light source 111 of the light output unit 110 is converted into a plurality of laser beams using a diffractive optical element 112.

The diffractive optical element 112 controls laser light entering the diffractive optical element by utilizing a light diffraction phenomenon. For example, as shown in FIG. 5, when laser light 41 output from the light source 111 enters the diffractive optical element 112, the laser light 41 is output in a plurality of directions by a light diffraction phenomenon. Thereafter, the laser light 41 is incident as a laser beam group 42 to an object 30. Thus, by using the diffractive optical element 112, a single beam of laser light 41 output from the light source 111 can be converted into a plurality of laser beams (laser beam group 42).

FIG. 6 shows an example in which laser light output from the light output unit 110 is a plurality of laser beams using a surface-emitting laser array 115.

For example, the surface-emitting laser array 115 outputs laser beams from a plurality of light sources on a light emission surface. Thereafter, the plurality of laser beams output from the plurality of light sources on the light emission surface are incident, as a laser beam group 51, to an object.

[Arrangement Example of Light Sources]

Here, it is assumed that the reflected light beams of laser beams output from a plurality of adjacent light sources in the surface-emitting laser array 115 are measured. In this case, it is also assumed that the regions (regions on a speckle pattern) of the reflected light beams of laser beams output from a plurality of adjacent light sources in the surface-emitting laser array 115 overlap. Thus, even when there is such an overlapping region, it is important to correctly measure the overlapping region.

Under these circumstances, an example is shown in FIG. 7 in which, in the surface-emitting laser array 115, light sources are arranged so that light sources for outputting laser beams having different wavelengths are adjacent to each other. Also, another example is shown in FIG. 8 in which, in the surface-emitting laser array 115, light sources are arranged so that light sources for outputting laser beams having different polarization directions (polarization angles) are adjacent to each other.

Figure 8:
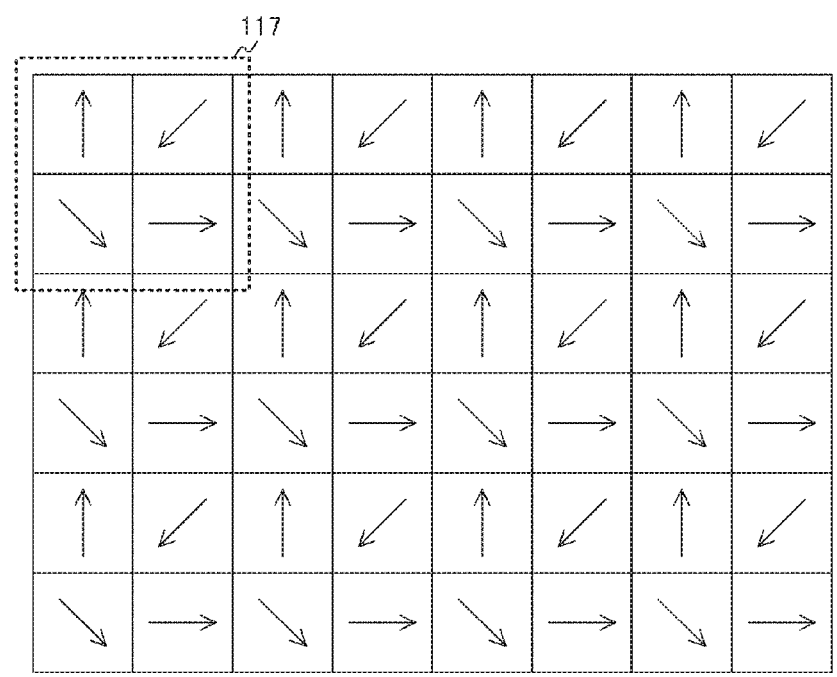
FIG. 8 is a diagram showing an arrangement example of light sources of a surface-emitting laser array 115 in an embodiment of the present technology.

FIG. 7 and FIG. 8 are diagrams showing arrangement examples of the light sources of the surface-emitting laser array 115 in the embodiment of the present technology. Note that FIG. 7 and FIG. 8 show an arrangement example of a portion of the light sources in the surface-emitting laser array 115, for the sake of simplicity. Also, in FIG. 7 and FIG. 8, a light source is schematically represented by a rectangle.

As shown in FIG. 7, in the surface-emitting laser array 115, the light sources can be arranged so that light sources for outputting laser beams having different wavelengths are adjacent to each other. Note that, in FIG. 7, different wavelengths are indicated by different letters in the rectangles representing the light sources.

For example, a first light source for outputting a laser beam having a first wavelength and a second light source for outputting a laser beam having a second wavelength which are arranged on a diagonal line, and two third light sources for outputting a laser beam having a third wavelength which are arranged on another diagonal line, constitute a unit. In FIG. 7, one unit is shown and surrounded by a dotted-line rectangle 116. Specifically, in the dotted-line rectangle 116, a first light source for outputting a red (R) laser beam and a second light source for outputting a blue (B) laser beam are arranged on a diagonal line, and two third light sources for outputting an infrared (IR) laser beam are arranged on another diagonal line. In this case, the light sources can be arranged so that the units are arranged in a grid pattern.

Also, as shown in FIG. 7, in the surface-emitting laser array 115, when light sources for outputting laser beams having different wavelengths are arranged, an image sensor capable of acquiring color information is used as the speckle image sensor 121 of the imaging unit 120. For example, an image sensor including color filters corresponding to the respective colors can be used.

Alternatively, as shown in FIG. 8, in the surface-emitting laser array 115, the light sources can be arranged so that light sources for outputting laser beams having different polarization directions (polarization angles) are adjacent to each other.

For example, a first light source for outputting a laser beam having a first polarization direction and a second light source for outputting a laser beam having a second polarization direction are arranged on a diagonal line, and a third light source for outputting a laser beam having a third polarization direction and a fourth light source for outputting a laser beam having a fourth polarization direction are arranged on another diagonal line. These light sources constitute a unit. In FIG. 8, one unit is shown and surrounded by a dotted-line rectangle 117. Also, in FIG. 8, a polarization direction is schematically represented by an arrow. In this case, the light sources can be arranged so that the units are arranged in a grid pattern.

Also, as shown in FIG. 8, in the surface-emitting laser array 115, when light sources for outputting light beams having different polarization directions are arranged, an image sensor capable of acquiring polarization information can be used as the speckle image sensor 121 of the imaging unit 120. For example, an image sensor including an array of polarizers corresponding to the respective polarization directions can be used.

Also, the light output unit 110 may modulate light (one or more light beams) output from a light source so that an overlapping portion of the regions (regions on a speckle pattern) of the reflected beams of a plurality of laser beams adjacent to each other can be correctly measured. In this case, adjacent laser beams are modulated to become different from each other. For example, the amplitude of light output from a light source can be modulated and output. Also, for example, the frequency of light output from a light source can be modulated and output.

Thus, a plurality of locations to which the light output unit 110 outputs light are arranged within the entirety or a portion of the imaging range of the object image sensor 122 of the imaging unit 120.

[Relationship Example Between Plurality of Laser Beams and Objects]

FIG. 9(a) and FIG. 9(b) to FIG. 11(a) and FIG. 11(b) are diagrams showing relationship examples between laser light output from the information processing apparatus 100 and objects in the embodiment of the present technology.

FIG. 9(a) and FIG. 9(b) shows a case example in which a scene is shot where three persons (persons 301 to 303) are talking together on stage for a play. FIG. 9a shows an image 300 included within the imaging range of the object image sensor 122. Also, FIG. 9b shows a display example in a case where marks (including black dots 311 to 313) indicating positions to which laser light is output from the light output unit 110 are superimposed over the image 300.

Thus, by outputting a plurality of laser beams from the light output unit 110 to objects (the image 300) which are within the imaging range of the object image sensor 122, an image of a speckle pattern can be acquired for a plurality of portions. For example, a voice of the person 301 can be acquired using a laser beam corresponding to the black dot 311. Similarly, a voice of the person 302 can be acquired using a laser beam corresponding to the black dot 312, and a voice of the person 303 can be acquired using a laser beam corresponding to the black dot 313. Thus, voices of a plurality of objects of interest can be simultaneously acquired.

Figure 10:
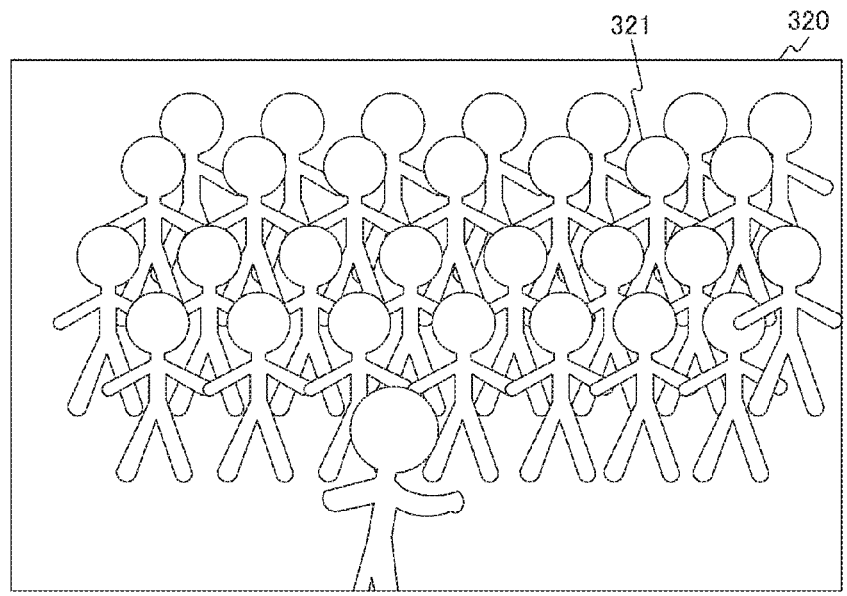
Figure 10:
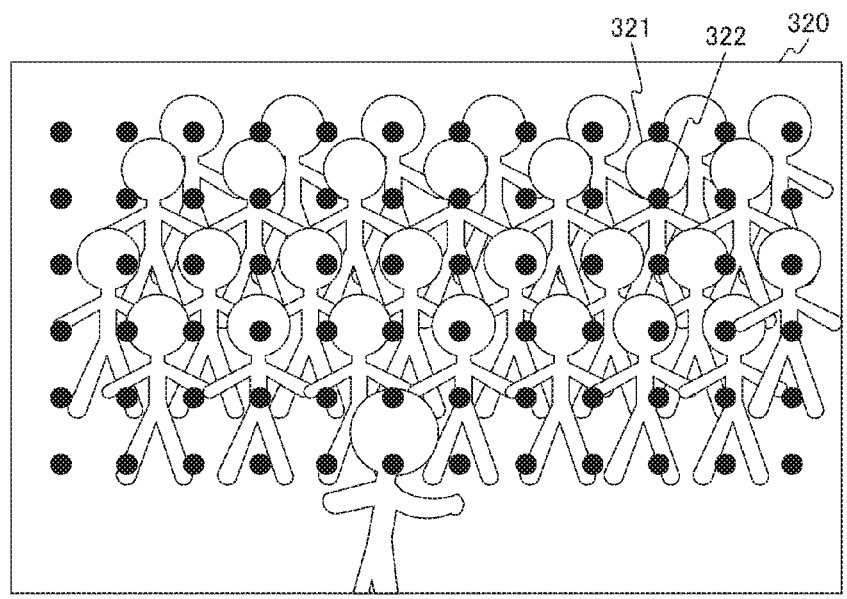

FIG. 10(a) and FIG. 10 (b) shows a case example in which pupils (including a person 321) in a class are singing in a school concert. FIG. 10a shows an image 320 included in the imaging range of the object image sensor 122. Also, FIG. 10b shows a display example in a case where marks (including a black dot 322) indicating positions to which laser light is output from the light output unit 110 are superimposed over the image 320.

For example, it is assumed that the person 321 is a child of a person (parent) who is shooting a moving image using the information processing apparatus 100. In this case, the parent can raise only a voice of their child (person 321) while lowering voices of the other persons. For example, a sound (a voice of the person 321) which is acquired on the basis of a laser beam corresponding to the black dot 322 can be raised. For example, it is assumed that the image 320 shown in FIG. 10b is displayed on the display unit 170 including a touchscreen. In this case, the user, when desiring to raise and record only a voice of the person 321, performs a touch operation on a portion corresponding to the black dot 322. When the touch operation is received by the operation reception unit 160, the control unit 190 can raise a voice (voice of the person 321) acquired on the basis of a laser beam corresponding to the black dot 322 at a position where the touch operation has been performed, and record the resultant voice into the storage unit 140.

Also, for example, similarly, when an image content stored in the storage unit 140 is played back, a voice of a desired person (e.g., a voice of the person 321) can be raised. For example, it is assumed that the image 320 shown in FIG. 10b is displayed on the display unit 170 including a touchscreen. In this case, the user, when desiring to raise and play back only a voice of the person 321, performs a touch operation on a portion corresponding to the black dot 322. When the touch operation is received by the operation reception unit 160, the control unit 190 can raise a voice (voice of the person 321) acquired on the basis of a laser beam corresponding to the black dot 322 at a position where the touch operation has been performed, and output the resultant voice from the audio output unit 180.

FIG. 11(a) and FIG. 11(b) shows an example of a case where the information processing apparatus 100 is used as a surveillance camera. FIG. 11a shows an image 330 included within the imaging range of the object image sensor 122. Also, FIG. 11b shows a display example of a case where marks (black dots) indicating positions to which laser light is output from the light output unit 110 are superimposed over the image 330.

Figure 11:
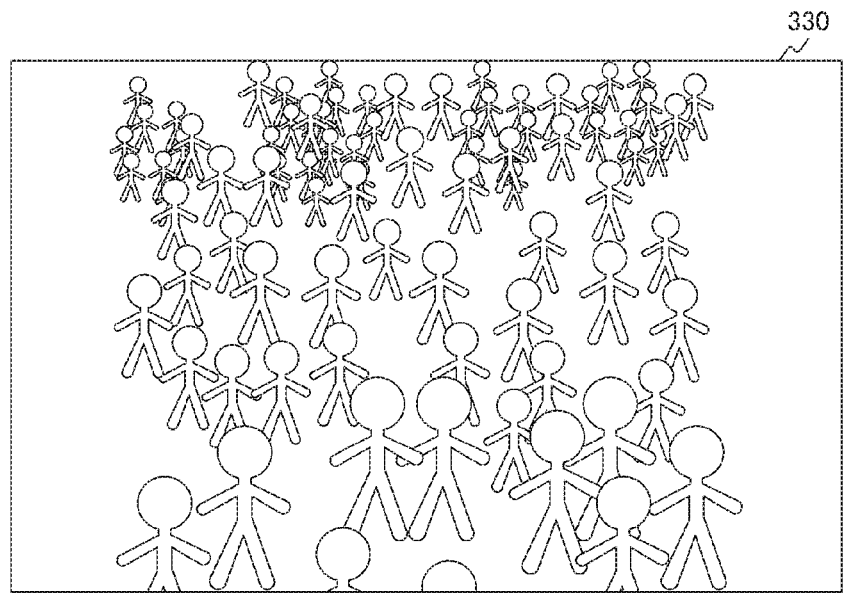
Figure 11:
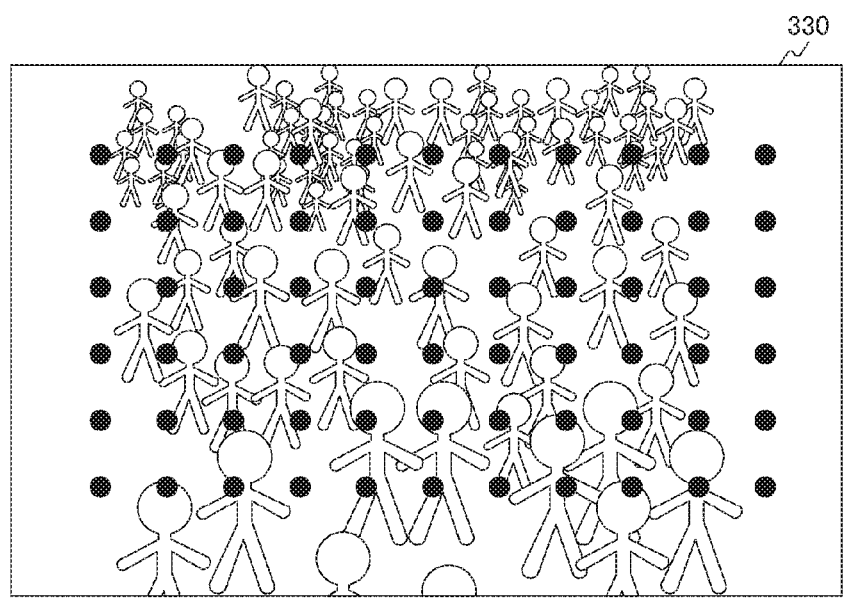

For example, it is assumed that the information processing apparatus 100 is installed so that a person walking on a sidewalk is within the imaging range. In this case, as shown in FIG. 11(a) and FIG. 11 (b), a plurality of persons moving on the sidewalk are contained in the image 330. Also, in this case, as in FIG. 10(a) and FIG. 10 (b), a voice of a desired person can be raised during shooting or playback.

Here, FIG. 11(a) and FIG. 11 (b) shows an example in which there is a large difference in distance (a distance from the information processing apparatus 100) between a person located closer to the information processing apparatus 100 (near the information processing apparatus 100) and a person farther away from the information processing apparatus 100 (opposite the information processing apparatus 100). In such a case, a speckle pattern based on a laser beam reflected from the closer person and a speckle pattern based on a laser beam from the farther person have different focal point positions. However, even in such a case, speckle patterns based on laser beams reflected from a plurality of objects (e.g., persons) located within a predetermined range can be used in analysis or the like even when they are slightly out of focus. Under these circumstances, in the example shown in FIG. 11(a) and FIG. 11 (b), image data of each speckle pattern can be generated and used while focusing on the speckle pattern of an object located in the vicinity of the center, for example. Note that the predetermined range is, for example, a distance range of 5 m to 20 m from the information processing apparatus 100. Note that the predetermined range shown here is merely illustrative, and can be set as appropriate, depending on the performance or the like of the information processing apparatus 100.

Figure 9:
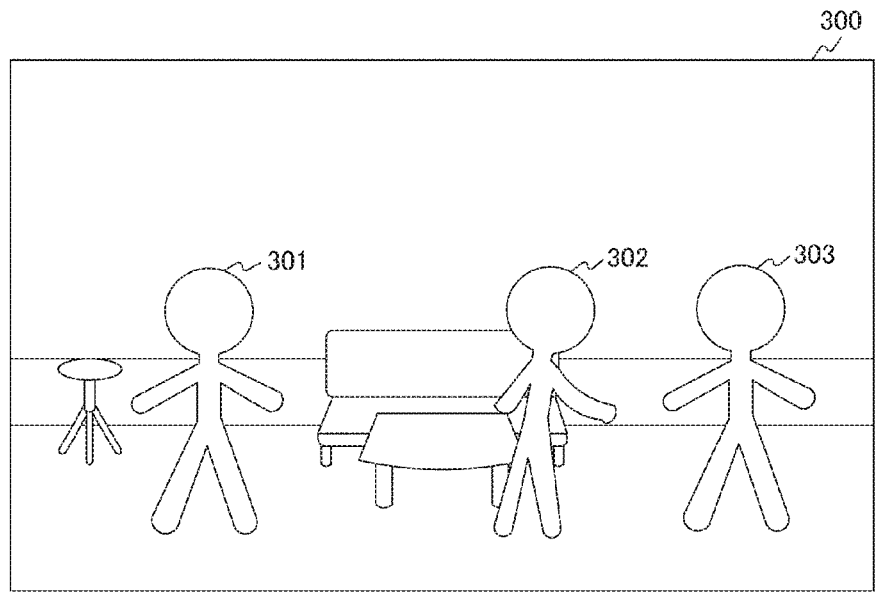
FIG. 9 (a) and FIG. 9 (b) is a diagram showing a relationship example between laser light output from an information processing apparatus 100 and objects in an embodiment of the present technology.
Figure 9:
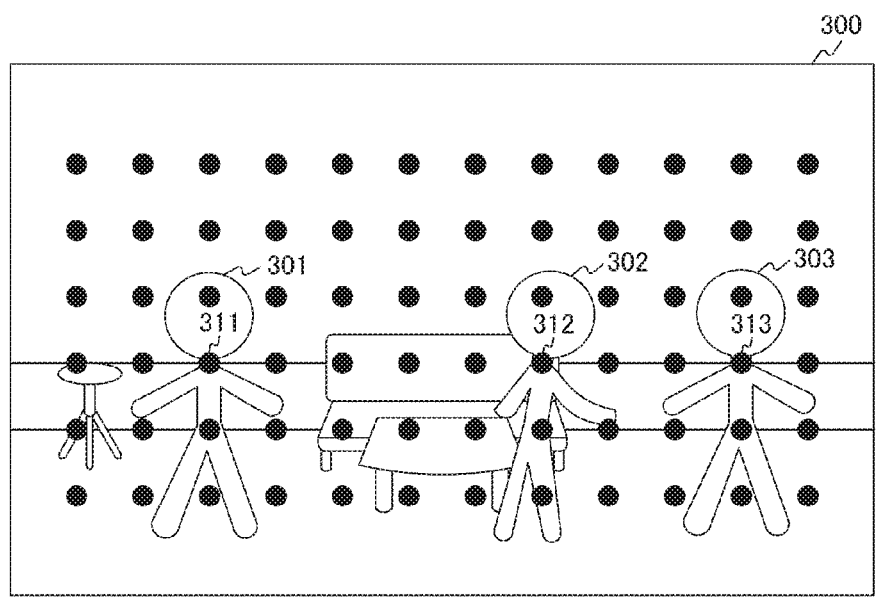

Note that although, in FIG. 9(a) and FIG. 9 (b) to FIG. 11(a) and FIG. 11 (b), the output positions of laser beams output from the light output unit 110 are arranged in a grid pattern within the imaging range of the object image sensor 122, other arrangements may be made. Alternatively, the output positions of a plurality of laser beams may be concentrated in a specific portion (e.g., a center portion) within the imaging range of the object image sensor 122. By thus causing the output positions of a plurality of laser beams to be dense, the accuracy of sound information acquired from the specific portion can be increased.

Also, imaging control can be performed using various kinds of information acquired on the basis of an oscillation in a speckle pattern (e.g., sound data, distance information). For example, it is assumed that sound data of a person which is within the imaging range has been acquired on the basis of an oscillation in a speckle pattern. In this case, the control unit 190 can perform control so that a position where the sound data has been acquired (a position within the imaging range) is designated as an auto focus (AF) area. Also, the control unit 190 can perform control so that a position where the sound data has been acquired (a position within the imaging range) is designated as an auto exposure (AE) area. In this case, for example, the setting of the AF area, the setting of the AE area, and the like may be performed under a condition that the face of a person has been detected at a position where the sound data has been acquired (a position within the imaging range). Alternatively, another condition that a specific object (e.g., a cat, dog, automobile, train) has been detected using another object detection function may be employed.

Also, for example, it is assumed that distance information of a person which is within the imaging range has been calculated on the basis of an oscillation in a speckle pattern. In this case, the control unit 190 can perform control so that a position (position within the imaging range) where the distance information has been calculated is designated as an AF area. Also, the control unit 190 can perform control so that a position (position within the imaging range) where the distance information has been calculated is designated as an auto exposure (AE) area. Also in this case, the detection of a specific object (e.g., a cat, dog, automobile, train) using an object detection function may be employed as a condition for the setting of the AF area, the setting of the AE area, or the like.

Thus, the control unit 190 can perform auto focus control or exposure control on the imaging unit 120 on the basis of at least one of sound data acquired on the basis of an oscillation in a speckle pattern, and the calculated distance information. Also, such imaging control allows continuation of AF and AE for a person uttering a voice, for example.

[Operation Example of Information Processing Apparatus]

Figure 12:
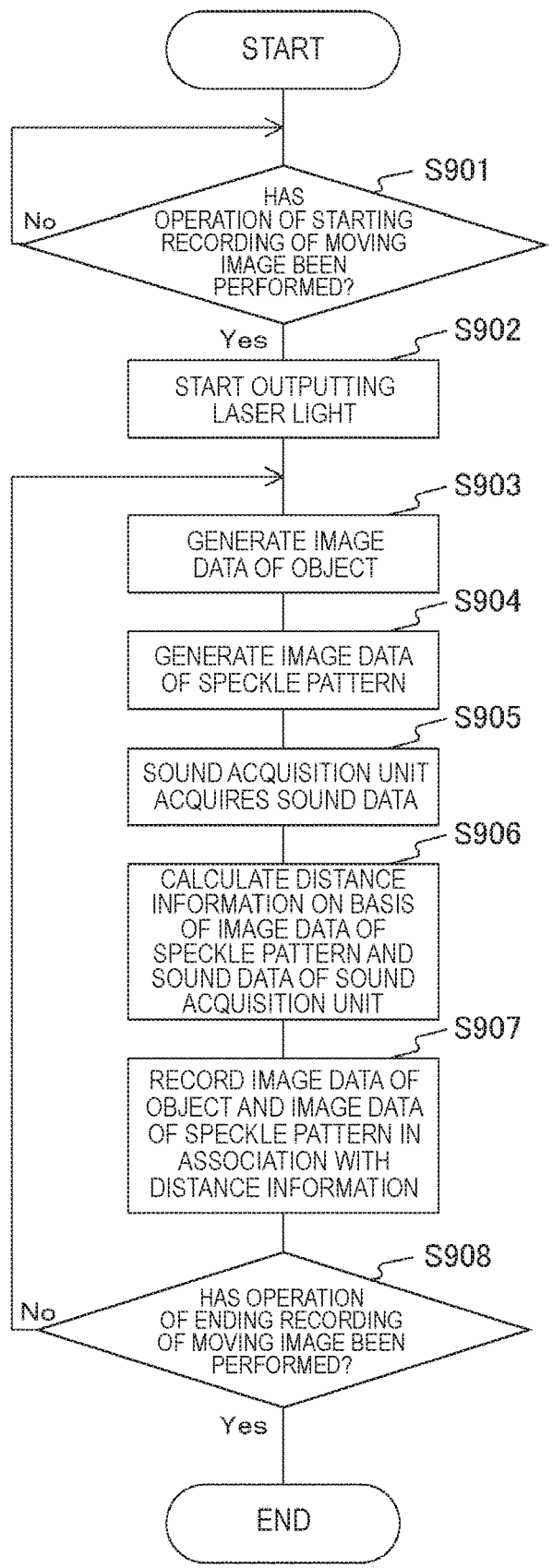
FIG. 12 is a flowchart showing an example of steps of a moving image recording process performed by an information processing apparatus 100 in an embodiment of the present technology.

FIG. 12 is a flowchart showing an example of steps of a moving image recording process performed by the information processing apparatus 100 in the embodiment of the present technology. FIG. 12 shows an example in which distance information is calculated during recording of a moving image.

Initially, the control unit 190 determines whether or not an operation of starting recording of a moving image has been performed (step S901). If the operation of starting recording of a moving image has not been performed (step S901), surveillance is continued.

If the operation of starting recording of a moving image has been performed (step S901), the light output unit 110 starts outputting light under the control of the control unit 190 (step S902). Note that step S902 is a light output step described in the accompanying claims.

Next, the object image sensor 122 of the imaging unit 120 and the object signal processing unit 132 of the signal processing unit 130 start generating image data of an object under the control of the control unit 190 (step S903). Similarly, the speckle image sensor 121 of the imaging unit 120 and the speckle signal processing unit 131 of the signal processing unit 130 start generating image data of a speckle pattern under the control of the control unit 190 (step S904). Note that step S904 is an example of an acquisition step described in the accompanying claims. Also, the sound acquisition unit 150 starts acquiring sound data under the control of the control unit 190 (step S905). Note that although, in FIG. 12, an example is shown in which the generation of image data of an object, the generation of image data of a speckle pattern, and the acquisition of sound data are sequentially performed, these processes may be performed simultaneously or in a different order.

Next, the control unit 190 calculates distance information on the basis of the image data of the speckle pattern and the sound data acquired by the sound acquisition unit 150 (step S906). Next, the control unit 190 records, into the storage unit 140, the image data of the object, the image data of the speckle pattern, and the calculated distance information in association with each other (step S907).

Note that although, in FIG. 12, an example is shown in which image data of a speckle pattern is recorded, sound data may be generated on the basis of image data of a speckle pattern, and the sound data may be recorded in association with the image data of the speckle pattern. Alternatively, sound data generated on the basis of image data of a speckle pattern and sound data acquired by the sound acquisition unit 150 may be recorded in association with each other. In this case, any one of these items of sound data may be used to correct the other item of sound data, which is then recorded.

Next, the control unit 190 determines whether or not an operation of ending recording of a moving image has been performed (step S908). If the operation of ending recording of a moving image has not been performed (step S908), control returns to step S903. Meanwhile, if the operation of ending recording of a moving image has been performed (step S908), the operation of the moving image recording process is ended.

Thus, the light output unit 110 outputs a plurality of light beams for generating a speckle pattern, to a plurality of locations of objects which are within the imaging range of the imaging unit 120. Also, the speckle image sensor 121 of the imaging unit 120 acquires image data of speckle patterns formed by scattering of the plurality of light beams striking the plurality of locations, on a location-by-location basis.

[Operation Example of Information Processing Apparatus]

Figure 13:
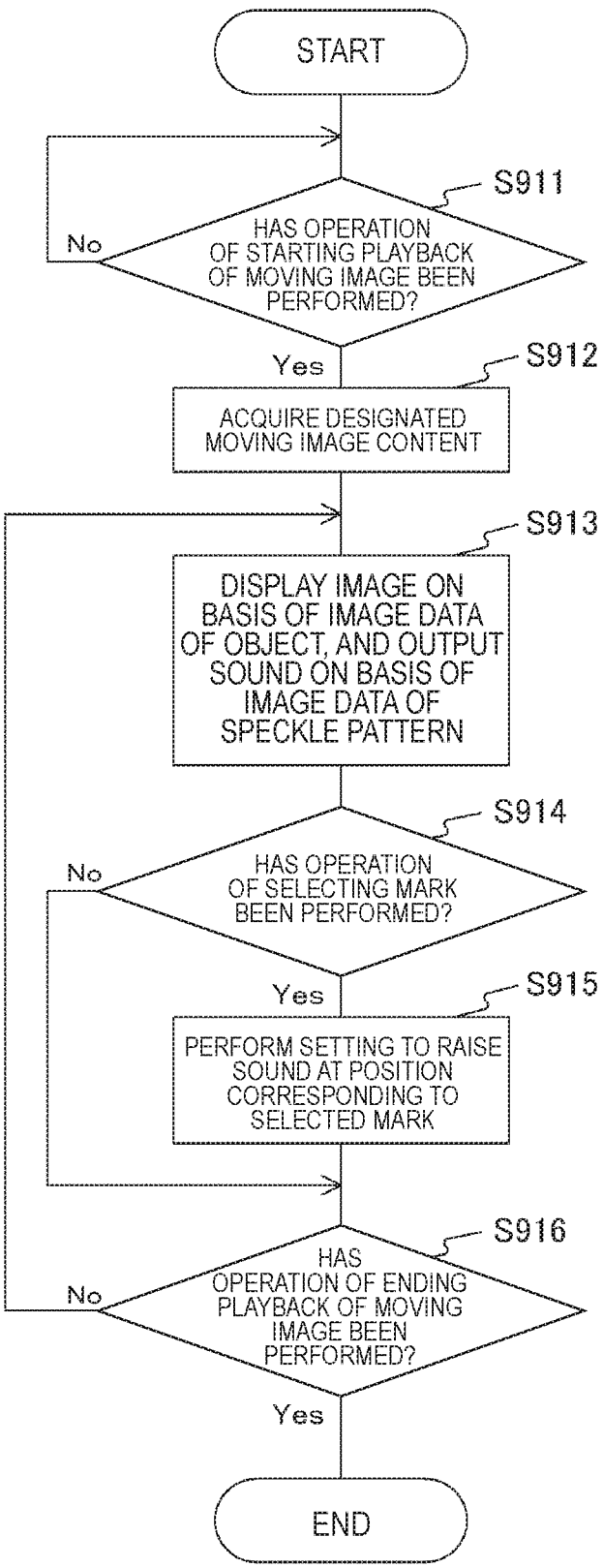
FIG. 13 is a flowchart showing an example of steps of a moving image playback process performed by an information processing apparatus 100 in an embodiment of the present technology.

FIG. 13 is a flowchart showing an example of steps of a moving image playback process performed by the information processing apparatus 100 in the embodiment of the present technology.

Initially, the control unit 190 determines whether or not an operation of starting playback of a moving image has been performed (step S911). If the operation of starting playback of a moving image has not been performed (step S911), surveillance is continued.

If the operation of starting playback of a moving image has been performed (step S911), the control unit 190 acquires, from the storage unit 140, a moving image content designated by the playback starting operation and each item of information associated with the moving image content (step S912). Note that the items of information associated with a moving image content are, for example, image data of a speckle pattern, sound data, and distance information.

Next, the control unit 190 causes the display unit 170 to display an image on the basis of image data contained in the moving image content (step S913). In this case, the control unit 190 displays and superimposes marks indicating the output positions of laser beams output from the light output unit 110 during recording of the image data (e.g., the black dots 311 to 313 shown in FIG. 9b) over an image to be displayed. For example, marks are displayed as shown in FIG. 9b, FIG. 10b, and FIG. 11b.

Also, the control unit 190 generates sound data on the basis of image data of a speckle pattern associated with the moving image content, and outputs the sound data from the audio output unit 180 (step S913). Note that when the sound data is associated with the moving image content, the sound data may be output from the audio output unit 180.

Next, the control unit 190 determines whether or not an operation of selecting a mark has been performed (step S914). If the operation of selecting a mark has not been performed (step S914), control proceeds to step S916.

If the operation of selecting a mark has been performed (step S914), the control unit 190 performs setting to raise sound generated at a position corresponding to the mark selected by the selection operation (step S915). Specifically, the control unit 190 performs setting to raise sound data which is generated on the basis of a speckle pattern of a laser beam which is output to a position corresponding to the mark selected by the selection operation (step S915).

Next, the control unit 190 determines whether or not an operation of ending playback of a moving image has been performed (step S916). If the operation of ending playback of a moving image has not been performed (step S916), control returns to step S913. Meanwhile, if the operation of ending playback of a moving image has been performed (step S916), the operation of the moving image playback process is ended.

Thus, the control unit 190 can acquire and output sounds generated at a plurality of locations on a location-by-location basis, on the basis of image data of speckle patterns formed by scattering of light beams striking a plurality of locations which are within the imaging range of the imaging unit 120. Also, when a selection operation of selecting a desired location from a plurality of locations has been received, the control unit 190 can acquire and output only a sound generated at the selected location.

Thus, in the embodiment of the present technology, for example, a plurality of focal points of laser beams are used to cover the entirety (or a portion) of the imaging range, whereby speckle patterns occurring a plurality of locations can be acquired. As a result, sound data of a plurality of objects of interest can be simultaneously acquired. Also, of objects of interest illuminated by laser light, only sound data of a desired object of interest can be easily extracted during or after shooting (e.g., during playback).

Thus, according to the embodiment of the present technology, a speckle pattern can be effectively utilized. Also, a multi-spot optical microphone can be implemented.

Note that, in the embodiment of the present technology, an example has been shown in which a single information processing apparatus includes an imaging unit for generating image data of an object and an imaging unit for generating image data of a speckle pattern. Note that the imaging unit for generating image data of an object and the imaging unit for generating image data of a speckle pattern may be provided in different apparatuses. In this case, image data generated by each apparatus can be recorded in association in that apparatus.

The above-described embodiments are examples for embodying the present technology, and matters in the embodiments each have a corresponding relationship with disclosure-specific matters in the claims. Likewise, the matters in the embodiments and the disclosure-specific matters in the claims denoted by the same names have a corresponding relationship with each other. However, the present technology is not limited to the embodiments, and various modifications of the embodiments may be embodied in the scope of the present technology without departing from the spirit of the present technology.

The processing sequences that are described in the embodiments described above may be handled as a method having a series of sequences or may be handled as a program for causing a computer to execute the series of sequences and recording medium storing the program. As the recording medium, a CD (Compact Disc), an MD (MiniDisc), and a DVD (Digital Versatile Disc), a memory card, and a Blu-ray (registered trademark) disc can be used.

In addition, the effects described in the present specification are not limiting but are merely examples, and there may be additional effects.

Additionally, the present technology may also be configured as below.

(1)
An information processing apparatus including:
a light output unit configured to output a plurality of light beams for generating speckle patterns, to a plurality of locations of objects which are within an imaging range; and
an acquisition unit configured to acquire the speckle patterns formed by scattering of the plurality of light beams striking the plurality of locations, on a location-by-location basis.

(2)
The information processing apparatus according to (1), wherein
the light output unit outputs a single beam of light that is output from a light source, as the plurality of light beams by using a diffractive optical element.

(3)
The information processing apparatus according to (1), wherein
the light output unit outputs a plurality of laser beams by using a laser array as a light source.

(4)
The information processing apparatus according to (3), wherein
the light output unit uses a surface-emitting laser array as the laser array.

(5)
The information processing apparatus according to (3) or (4), wherein
the light output unit outputs the plurality of laser beams having different wavelengths from the laser array, and
the acquisition unit acquires the speckle patterns by using an image sensor capable of acquiring color information.

(6)
The information processing apparatus according to (3) or (4), wherein
the light output unit outputs the plurality of laser beams having different polarization directions from the laser array, and
the acquisition unit acquires the speckle patterns by using an image sensor capable of acquiring polarization information.

(7)
The information processing apparatus according to any of (2) to (4), wherein
the light output unit modulates the plurality of light beams and outputs the plurality of modulated light beams from the light source.

(8)
The information processing apparatus according to any of (1) to (7), wherein
the plurality of locations are arranged in the entirety or a portion of the imaging range.

(9)
The information processing apparatus according to any of (1) to (8), further including:
a control unit configured to acquire at least one of sound data and distance information related to the object on the basis of the acquired speckle pattern.

(10)
The information processing apparatus according to any of (1) to (8), further including:
an imaging unit configured to image the object to generate image data; and
a control unit configured to acquire at least one of sound data and distance information related to the object on the basis of the acquired speckle pattern,
wherein
the control unit performs auto focus control on the imaging unit on the basis of at least one of the acquired sound data and the acquired distance information.

(11)
The information processing apparatus according to any of (1) to (8), further including:
an imaging unit configured to image the object to generate image data; and
a control unit configured to acquire at least one of sound data and distance information related to the object on the basis of the acquired speckle pattern,
wherein
the control unit performs exposure control on the imaging unit on the basis of at least one of the acquired sound data and the acquired distance information.

(12)
The information processing apparatus according to any of (1) to (8), further including:
a sound acquisition unit configured to acquire sound data around the information processing apparatus on the basis of vibration of a substance; and
a control unit configured to acquire sound data related to the object on the basis of the acquired speckle pattern, and calculate a distance between the information processing apparatus and the object on the basis of the sound data related to the object and the sound data acquired by the sound acquisition unit.

(13)
An information processing apparatus including:
a control unit configured to calculate a distance between the information processing apparatus and an object which is within an imaging range, on the basis of sound data related to the object acquired on the basis of a speckle pattern formed by scattering of light striking the object, and sound data related to the object acquired on the basis of vibration of a substance.

(14)
An information processing apparatus including:
a control unit configured to acquire and output sounds generated at a plurality of locations of objects which are within an imaging range on a location-by-location basis, on the basis of speckle patterns formed by scattering of light beams striking the plurality of locations.

(15)
The information processing apparatus according to (14), wherein
when a selection operation of selecting a desired location from the plurality of locations has been received, the control unit acquires and outputs only a sound generated at the selected location.

(16)
An information processing method including:
a light output step of outputting a plurality of light beams for generating speckle patterns, to a plurality of locations of objects which are within an imaging range; and
an acquisition step of acquiring the speckle patterns formed by scattering of the plurality of light beams striking the plurality of locations, on a location-by-location basis.

(17)
A program for causing a computer to execute:
a light output step of outputting a plurality of light beams for generating a speckle patterns, to a plurality of locations of objects which are within an imaging range; and
an acquisition step of acquiring the speckle patterns formed by scattering of the plurality of light beams striking the plurality of locations, on a location-by-location basis.

REFERENCE SIGNS LIST 100 information processing apparatus
110 light output unit
111 light source
112 diffractive optical element
115 surface-emitting laser array
120 imaging unit
121 speckle image sensor
122 object image sensor
123, 124 optical system
130 signal processing unit
131 speckle signal processing unit
132 object signal processing unit
140 storage unit
150 sound acquisition unit
160 operation reception unit
170 display unit
180 audio output unit
190 control unit
200 imaging unit
201 speckle image sensor
202 object image sensor
203 optical system
204 half mirror

The invention claimed is:

1. An information processing apparatus, comprising:
a light output unit configured to output, to a plurality of locations, a plurality of light beams to generate speckle patterns, wherein
the plurality of locations corresponds to a plurality of objects, and
each of the plurality of objects is within an imaging range of the information processing apparatus;
an acquisition unit configured to acquire the speckle patterns for each of the plurality of locations,
wherein the speckle patterns are based on scatter of the plurality of light beams that strikes the plurality of locations;
a sound acquisition unit configured to acquire first sound data in proximity of the information processing apparatus,
wherein the first sound data is based on vibration of a substance associated with a specific object of the plurality of objects; and
a control unit configured to:
acquire second sound data based on the acquired speckle patterns; and
calculate a distance between the information processing apparatus and the specific object based on the first sound data and the second sound data, wherein the second sound data is associated with the specific object.

2. The information processing apparatus according to claim 1, wherein the light output unit comprises:
a light source configured to output a single beam of light; and
an optical diffraction element configured to convert the single beam of light to the plurality of light beams.

3. The information processing apparatus according to claim 1, wherein
the light output unit comprises a laser array as a light source,
the laser array is configured to generate a plurality of laser beams, and
the light output unit is further configured to output the plurality of laser beams.

4. The information processing apparatus according to claim 3, wherein the laser array is a surface-emitting laser array.

5. The information processing apparatus according to claim 3, wherein
the light output unit is further configured to output the plurality of laser beams, wherein a wavelength of each of the plurality of laser beams is different, and
the acquisition unit comprises an image sensor configured to:
acquire color information associated with the plurality of laser beams; and
acquire the speckle patterns based on the color information.

6. The information processing apparatus according to claim 3, wherein
the light output unit is further configured to output the plurality of laser beams, wherein a polarization direction of each of the plurality of laser beams is different, and
the acquisition unit comprises an image sensor configured to:
acquire polarization information associated with the plurality of laser beams; and
acquire the speckle patterns based on the polarization information.

7. The information processing apparatus according to claim 3, wherein the light output unit is further configured to:
modulate the plurality of light beams; and
output the modulated plurality of light beams from the light source.

8. The information processing apparatus according to claim 1, wherein
the plurality of locations is in entirety of the imaging range or a portion of the imaging range.

9. The information processing apparatus according to claim 1, wherein
the control unit is further configured to acquire at least one of the second sound data or distance information based on the acquired speckle patterns, and
each of the second sound data and the distance information is associated with the specific object.

10. The information processing apparatus according to claim 1, further comprising an imaging unit configured to generate image data based on the specific object, wherein
the control unit is further configured to:
acquire at least one of the second sound data or distance information based on the acquired speckle patterns; and
control focus of the imaging unit based on at least one of the acquired second sound data or the acquired distance information, and
each of the second sound data and the distance information is associated with the specific object.

11. The information processing apparatus according to claim 1, further comprising an imaging unit configured to generate image data based on the specific object, wherein
the control unit is further configured to:
acquire at least one of the second sound data or distance information based on the acquired speckle patterns; and
control exposure of the imaging unit based on at least one of the acquired second sound data or the acquired distance information, and
each of the second sound data and the distance information is associated with the specific object.

12. An information processing apparatus, comprising:
a sound acquisition unit configured to acquire first sound data in proximity of the information processing apparatus,
wherein the first sound data is based on vibration of a substance associated with a specific object of a plurality of objects;
a control unit configured to:
acquire second sound data generated at a specific location of a plurality of locations, wherein
the second sound data is acquired based on speckle patterns for the specific location,
the plurality of locations corresponds to the plurality of objects,
the specific location corresponds to the specific object of the plurality of objects,
each of the plurality of objects is within an imaging range of the information processing apparatus, and
the speckle patterns are based on scatter of light beams that strike the plurality of locations; and
calculate a distance between the information processing apparatus and the specific object based on the first sound data and the second sound data.

13. The information processing apparatus according to claim 12, wherein the control unit is further configured to:
receive a selection operation to select a desired location from the plurality of locations; and
acquire and output a specific sound generated at the desired location of the plurality of locations.

14. An information processing method, comprising:
outputting, to a plurality of locations, a plurality of light beams for generating speckle patterns, wherein
the plurality of locations corresponds to a plurality of objects, and
each of the plurality of objects is within an imaging range of an information processing apparatus;
acquiring the speckle patterns for each of the plurality of locations,
wherein the speckle patterns are based on scatter of the plurality of light beams that strikes the plurality of locations;
acquiring first sound data in proximity of the information processing apparatus,
wherein the first sound data is based on vibration of a substance associated with a specific object of the plurality of objects; and
acquiring second sound data based on the acquired speckle patterns, and
calculating a distance between the information processing apparatus and the specific object based on the first sound data and the second sound data, wherein the second sound data is associated with the specific object.

15. A non-transitory computer-readable medium having stored thereon computer-executable instructions which, when executed by a computer, cause the computer to execute operations, the operations comprising:
outputting, to a plurality of locations, a plurality of light beams for generating speckle patterns, wherein
the plurality of locations corresponds to a plurality of objects, and
each of the plurality of objects is within an imaging range of an information processing apparatus;
acquiring the speckle patterns for each of the plurality of locations,
wherein the speckle patterns are based on scatter of the plurality of light beams that strikes the plurality of locations;
acquiring first sound data in proximity of the information processing apparatus,
wherein the first sound data is based on vibration of a substance associated with a specific object of the plurality of objects; and
acquiring second sound data based on the acquired speckle patterns; and
calculating a distance between the information processing apparatus and the specific object based on the first sound data and the second sound data, wherein the second sound data is associated with the specific object.

* * * * *